United States Patent
Gilbert et al.

(10) Patent No.: US 6,709,834 B2
(45) Date of Patent: Mar. 23, 2004

(54) **LIPOPOLYSACCHARIDE α-2,3 SIALYTRANSFERASE OF *CAMPYLOBACTER JEJUNI* AND ITS USES**

(75) Inventors: Michel Gilbert, Quebec (CA); Warren W. Wakarchuk, Ontario (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 10/058,636

(22) Filed: Jan. 29, 2002

(65) Prior Publication Data

US 2003/0049270 A1 Mar. 13, 2003

Related U.S. Application Data

(62) Division of application No. 09/272,960, filed on Mar. 18, 1999.
(60) Provisional application No. 60/078,891, filed on Mar. 20, 1998, now abandoned.

(51) Int. Cl.[7] .................................................. C12Q 1/48
(52) U.S. Cl. ............................... 435/15; 435/6; 435/97; 435/4; 435/7.2; 435/41; 435/183; 435/193; 435/252.3; 435/220; 435/320.1; 435/85; 530/350
(58) Field of Search .......................... 435/6, 85, 320.1, 435/57, 4, 7.2, 15, 41, 183, 193, 252.3, 220; 530/350

(56) References Cited

U.S. PATENT DOCUMENTS

| | | | |
|---|---|---|---|
| 5,352,670 A | 10/1994 | Venot et al. | |
| 5,374,541 A | 12/1994 | Wong et al. | |
| 5,494,790 A | * 2/1996 | Sasaki et al. | 435/6 |
| 5,545,553 A | 8/1996 | Gotschlich | |
| 5,691,138 A | 11/1997 | Guesdon et al. | |
| 5,998,138 A | 12/1999 | Stonnet et al. | |
| 6,096,529 A | * 8/2000 | Gilbert et al. | 435/252.3 |
| 6,399,336 B1 | * 6/2002 | Paulson et al. | 435/97 |

FOREIGN PATENT DOCUMENTS

| | | |
|---|---|---|
| EP | 173149 A | 3/1986 |
| WO | WO 96/32491 | 10/1996 |
| WO | WO 97/477499 | 12/1997 |
| WO | WO 98/31826 | 7/1998 |

OTHER PUBLICATIONS

Weiser, et al. *Critical Review in Clinical Laboratory Sciences*, (Jun. 1981) vol. 14(3), pp. 189–239.

Weisgerber et al., "Complete nucleotide and deduced protein sequence of CMP–neuAc: poly–a–2,8 sialosyl sialyltransferase of *Escherichia coli* K1," Glycobiol. 1:357–365 (1991).

Williams et al., "Large–scale expression of recombinant sialyltransferases and comparison of their kinetic properties with native enzymes," *Glycoconjugate J*. 12: 755–761.

Wakarchuk et al., "Mutational and crystallographic analyses of the active site residues of the *Bacillus circulans* xylanase," *Protein Sci*. 3:467–475.

Yamamoto et al., "Purification and Characterization of a Marine Bacterial B–Galactoside a2,6–Sialyltransferase from *Photobacterium damsela* JT0160," *J. Biochem*. 120:104–110 (1996).

Yamamoto, et al. *J. of Biochemistry*, (Jan. 1998) vol. 123(1), pp. 94–100.

(List continued on next page.)

*Primary Examiner*—Lynette R. F. Smith
*Assistant Examiner*—Ginny Allen Portner
(74) *Attorney, Agent, or Firm*—Townsend and Townsend and Crew LLP

(57) ABSTRACT

The structure and specificity of a recombinant α2,3-sialyltransferase from *Campylobacter* spp., is disclosed. Also provided are methods for using the α2,3-sialyltransferase in the production of desired carbohydrate structures and nucleic acids that encode the sialyltransferase.

15 Claims, 4 Drawing Sheets

```
CST-I  MTRTRMENELIVSKNMQNIIIAGNGPSLKNINYKRLPREYDVFRCNQFYFEDKYYLGKKI   60

CST-I  KAVFFNPGVFLQQYHTAKQLILKNEYEIKNIFCSTF-NLPFIESNDFLHQFYNFFPDAKL  119
       ||| ||||  |  | ||| |
HIN              MQLIKNNEYEYADIILSSFVNLGDSELKK-IKNVQKLLTQVDI   42

CST-I  GYEVIENLKEFYAYIKYNEIYFNKRITSGVYMCAIAIALGYKTIYLCGIDFY-EGDVIYP  178
       |  |  ||  |||  |  | |||||||||| |  ||  || ||||  |
HIN    GHYYLNKLPAFDAYLQYNELYENKRITSGVYMCAVATVMGYKDLYLTGIDFYQEKGNPYA  102

CST-I  FEAMSTNIKTIFPGIKDFKP-SNCHSKEYDIEALKLLKSIYKVNIYALCDDSILANHFPL  237
       |  ||    | |    |  | |  ||  ||  ||   |  ||||       ||| |||
HIN    FHHQKENIIKLLPSFSQNKSQSDIHSMEYDLNALYFLQKHYGVNIYCISPESPLCNYFPL  162

CST-I  S-ININNNFTLENKHNNSINDILLTDNTPGVSFYKNQLKADNKIMLNFYNILHSKDNLIK  296
       |   |    | ||||   |  |||         | |      ||    ||   |||
HIN    SPLNNPITFILEEKKNYT-QDILI----PPKFVYK------KIGI--YSKPRIYQNLIF  208

CST-I  FLNKEIAVLKKQTTQRAKARIQNHLSYKLGQALIINSKSVLGFLSLPFIILSIVISHKQE  356
       |       |  |    ||
HIN    RLIWDILRLPNDIKHALKSRKWD                                      231

CST-I  QKAYKFKVKKNPNLALPPLETYPDYNEALKEKECFTYKLGEEFIKAGKNWYGEGYIKFIP  416

CST-I  KDVPRLKREFEKGE                                               430
```

OTHER PUBLICATIONS

Yamashiro, et al. *Glycoconjugate Journal*, (Dec. 1995) vol. 12(6), pp. 894–900.

Preston et al., "The Lipooligosaccharides of Pathogenic Gram–Negative Bacteria," *Crit. Rev. Microbiol.* 22:139–180.

Rest, et al. *Microbial Pathogenesis*, (1995) vol. 19(6), pp. 379–390.

Reuter et al., "Sialic Acids Structure—Analysis—Metabolism—Occurrence—Recognition," *Biol. Chem. Hoppe–Seyler* 377:325–342.

Roberts et al., Generation of an antibody with enhanced *Nature* 328:731–734 (1987).

Ropper, "The Guillain–Barre Syndrome," *N. Engl. J. Med.* 326: 1130–1136.

Salloway, et al. *Infection Immunity*, (Aug. 1996) vol. 64(8), pp. 2945–2949.

Smith, et al., *Microbial Pathogenesis*, (1995) vol. 19(6), pp. 365–377.

Steenbergen, et al., *Journal of Biochemistry*, (Feb. 1998) vol. 174(4), pp. 1099–1108.

Skirrow, *Brit. Med. J. "Campylobacter* enteritis: a 'new' disease," 2:9–11 (1977).

Taylor, et al. *Antimicrobial Agents & Chemotherapy* (Dec. 1983), vol. 24(6), pp. 930–935, (abstract only).

Taylor, et al. *Antimicrobial Agents and Chemotherapy*, (May 1981) vol. 19(5), pp. 831–835 (abstract only).

Varki, "Biological Roles of Oligosaccharides: all of the theories are correct," *Glycobiology* 3:97–130.

Vogel, et al. *Medical Microbiology and Immunology*, (Oct. 1997) vol. 186(2–3), pp. 159–166.

Ito et al., *Pure Appl. Chem.*, "Synthesis of Bioactive sialosides,"65:753 (1993).

Jamieson, et al. *Comparative Biochemistry and Physiology*, (1993) vol. 105(1), pp. 29–33.

Kajihara et al., "A Novel a–2,6–Sialyltransferase: Transfer of Sialic Acid to Fucosyl and Sialyl Trisaccharides," *J. Org. Chem.* 61: 8632–8635.

Kleene et al., "Expression of Soluble Active Human B1, 4 Galactosyltransferase in *Saccharomyces cerevisiae*," *Biochem. Biophys. Res. Commun.* 201:160–167 (1994).

Klohs, et al. *Cancer Res.*, (1979) vol. 39(4), pp. 1231–1238.

Korolik, et al. *Microbiology*, (Nov. 1997) vol. 143(pt11), pp. 3481–3489.

Kuroki et al., "*Campylobacter jejuni* Strains from Patients with Guillain–Barre Syndrome Belong Mostly to Penner Serogroup 19 and Contain B–N–Acetylglucosamine Residues," *Ann Neurol* 33:243–247. (1993).

Mandrell, et al. *Immunobiology*, (1993) vol. 187(3–5), pp. 382–402.

Maskell, et al. *Mol. Microbiol.*, (1991) vol. 5(5), pp. 1013–1022, (abstract only).

Moran et al., "Molecular mimicry of host structures by bacterial lipopolysaccharides and its contribution to disease," *MS Immunol. Med. Microbiol.* 16:105–115 (1996).

Moran et al., "Molecular mimicry of host structures by lipopolysaccharides of *Campylobacter* and *Helicobacter* spp: implications in pathogenesis," *J. Endotoxin Res.* 3:521–531.

Nishiu et al., "Characterization of Rat N–Acetylglucosaminyltransferase I Expressed in *Escherichia coli*," *Biosci. Biotech. Biochem.* 59 (9):1750–1752 (1995).

Parsons, et al. *Microbial Pathogenesis*, (1993) vol. 14(4), pp. 329–335.

Aoki et al., "Analysis of the substrate binding sites of human galactosyltransferase by protein engineering," *EMBO J.* 9:3171–3178 (1990).

Aspinall et al., "Lipopolysaccharides of *Campylobacter jejuni* Serotype 0:19: Structures of Core Oligosaccharide Regions from the Serostrain and Two Bacterial Isolates from Patients with the Guillain–Barre Sundrome," *Biochemistry* 33: 241–249 (1994).

Aspinall, et al., "Lipopolysaccharides of *Campylobacter jejuni* Serotype O:19: Structures of 0 Antigen Chains from the Serostrain and Two Bacterial Isolates from Patients with the Guillain–Barre Syndrome," *Biochemistry* 33: 250–255 (1994).

Bradbury, et al. *J. of Clinical Microbiol.*, (Sep. 1985) vol. 22(3), pp. 339–346, (abstract only).

Chang, et al. *Glycobiology*, (May 1995) vol. 5(3), pp. 319–325.

Frosch et al., "Evidence for a common molecular origin of the capsule gene loci in Gramnegative bacteria expressing group II capsular polysaccharides," *Mol. Microbiol.* 5: 1251–1263 (1991).

Gilbert et al., "Cloning of the Lipooligosaccharide a–2–3–Sialyltransferase from the Bacteria Pathogens *Neisseria meningitidis* and *Neisseria gonorrhoeae*, " *J. Biol. Chem.*, 271:28271–28276 (1996).

Gilbert et al., "Characterization of a recombinant Neisseria meningitidis a–2,3–sialyltransferase and its acceptor specificity ," *Eur. J. Biochem.* , 249: 187–194 (1997).

Gilbert, et al. "The Synthesis of Sialylated Oligosaccharides Using a CMP–Neu5Ac Synthetase/sialyltransferase Fusion" *Nature Biotechnology* (Aug. 1998) vol. 16, pp. 769–772.

Gillam and Smith, "Site–Specific Mutagenesis Using Synthetic Oligodeoxyribonucleotide Primers: I. Optimum Conditions and Minimum Oligodeoxyribo–Nucleotide Length," *Gene* 8:81–97 (1979).

Guo, et al. *Applied Biochemistry and Biotechnology*, Oct.–Nov. 1997, vol. 68 (1–2), pp. 1–20.

Imai, et al. *Cytobios*, (1994) vol. 78(313), pp. 115–122 (abstract only).

Bowie et al. *Science* 257:1306–1310 (1990).

Burgess et al. *J. Cell Bio.* 111:2129–2138 (1990).

Lazar et al. *Mol. Cell. Biol* 8:1247–1252 (1988).

Yuki et al. *J. Neurological Sciences* 130:112–116 (1995).

* cited by examiner

Figure 2

```
nt#                                                                                              aa#
  1  ATGACAAGGACTAGAATGGAAAATGAACTCATTGTTAGTAAAAATATGCAAAATATAATCATAGCAGGAAATGGACCTAGCCTAAAAAAT
      M  T  R  T  R  M  E  N  E  L  I  V  S  K  N  M  Q  N  I  I  I  A  G  N  G  P  S  L  K  N    30

91  ATTAATTATAAAGACTGCCTAGAGAATGATGTTTTTAGGTGTAACCAGTTTTATTTGAAGATAAGTATTATTAGGAAAAAAGATT
      I  N  Y  K  R  L  P  R  E  Y  D  V  F  R  C  N  Q  F  Y  F  E  D  K  Y  Y  L  G  K  K  I    60

181  AAAGCAGTATTTTTTAATCCTGGTGTCTTTTTACAACAGTATCACACTGCAAAACAACTTATACTAAAAAATGAGTATGAAATAAAAAAT
      K  A  V  F  F  N  P  G  V  F  L  Q  Q  Y  H  T  A  K  Q  L  I  L  K  N  E  Y  E  I  K  N    90

271  ATTTTTTGCTCTACATTTAATTACCTTTTATTGAAAGCAATGATTTTTTACATCAATTTTATAATTTTTCCCGATGCAAAACTTGGC
      I  F  C  S  T  F  N  L  P  F  I  E  S  N  D  F  L  H  Q  F  Y  N  F  F  P  D  A  K  L  G   120

361  TATGAAGTTATTGAAAACCTTAAAGAATTTGCTTATATAAATACAATGAAATTTATTCAATAAAAGAATTACTTCGGGCGTCTAT
      Y  E  V  I  E  N  L  K  E  F  Y  A  Y  I  K  Y  N  E  I  Y  F  N  K  R  I  T  S  G  V  Y   150

451  ATGTGTGCAATTGCTATTGCATTAGGATATAAAACCATCTATTTATGTGGCATTGATTTTTATGAAGGAGATGTTATTATCCTTTTGAA
      M  C  A  I  A  I  A  L  G  Y  K  T  I  Y  L  C  G  I  D  F  Y  E  G  D  V  I  Y  P  F  E   180

541  GCTATGAGTACAAATATAAAAACAATCTTTCCTGGAATAAAAGATTTCAAACCTTCATTGTCATTCTAAGGAATACGATATAGAAGCA
      A  M  S  T  N  I  K  T  I  F  P  G  I  K  D  F  K  P  S  N  C  H  S  K  E  Y  D  I  E  A   210

631  TTAAAATTGTTAAAATCAATTTATAAAGTTAATAATCAAAGTTAATAATACAAAGCATTGTGATGATTCTATTTGGCAAATCATTTTCCTTTATCAATTAAT
      L  K  L  L  K  S  I  Y  K  V  N  I  Y  A  L  C  D  D  D  S  I  L  A  N  H  F  P  L  S  I  N   240

721  ATTAATAACAATTTCACTTTAGAAAATAAGCATAATTCTATAAATGATATTTTATTGACTGATAATACTCCTGGCGTAAGTTTTTAT
      I  N  N  F  T  L  E  N  K  H  N  S  I  N  D  I  L  L  T  D  N  T  P  G  V  S  F  Y   270

811  AAAAATCAACTTAAAGCTGATAATAAAATTATGCTTAATTTTTATAATATTCTTCATTCTAAAGATAATTAAATTTTTAAACAAA
      K  N  Q  L  K  A  D  N  K  I  M  L  N  F  Y  N  I  L  H  S  K  D  N  L  I  K  F  L  N  K   300
```

Figure 2 (continued)

```
 901 GAAATTGCGGGTATTAAAAAACAAACCACTCAACGAGCTAAAGCAAGAATCCAAAACCATCTATCCTATAAACTAGGACAAGCTTTGATT
      E  I  A  V  L  K  K  Q  T  T  Q  R  A  K  A  R  I  Q  N  H  L  S  Y  K  L  G  Q  A  L  I   330

991 ATAAAATTCTAAAAGTGTATTAGGTTTTTTATCTTTACCTTTTATAATATTAAGTATCGTTATTCACATAAACAAGAACAAGAAAGGCTTAT
      I  N  S  K  S  V  L  G  F  L  S  L  P  F  I  I  L  S  I  V  I  S  H  K  Q  E  Q  K  A  Y   360

1081 AAATTTAAAGTAAGAAAAAATCCAAATTTAGCTTTACCTCCTTTAGAACTTATCCTGATTATAATGAAGCTTTAAAAGAAAAAGAATGT
      K  F  K  V  K  K  N  P  N  L  A  L  P  P  L  E  T  Y  P  D  Y  N  E  A  L  K  E  K  E  C   390

1171 TTTACTTATAAATTAGGAGAAGAATTTATAAAAGCTGGTAAGAATTGGTATGGGGAGGGTATATCAAATTTATATTCAAAGATGTTCCT
      F  T  Y  K  L  G  E  E  F  I  K  A  G  K  N  W  Y  G  E  G  Y  I  K  F  I  F  K  D  V  P   420

1261 AGGTTGAAGAGAGAGTTTGAGAAAGGGGAATAA                                                      1293
      R  L  K  R  E  F  E  K  G  E  -                                                         430
```

Figure 3

```
CST-I  MTRTRMENELIVSKNMQNIIIAGNGPSLKNINYKRLPREYDVFRCNQFYFEDKYYLGKKI                    60
HIN                                                                                 119

CST-I  KAVFFNPGVFLQQYHTAKQLILKNEYEIKNIFCSTF-NLPFIESNDFLHQFYNFFPDAKL                    42
HIN                    MQLIKNNEYEYADIILSSFVNLGDSELKK-IKNVQKLLTQVDI

CST-I  GYEVIENLKEFYAYIKYNEIYFNKRITSGVYMCAIAIALGYKTIYLCGIDFY-EGDVIYP                    178
HIN    GHYYLNKLPAFDAYLQYNELYENKRITSGVYMCAVATVMGYKDLYLTGIDFYQEKGNPYA                    102

CST-I  FEAMSTNIKTIFPGIKDFKP-SNCHSKEYDIEALKLLKSIYKVNIYALCDDSILANHFPL                    237
HIN    FHHQKENIIKLLPSFSQNKSQSDIHSMEYDLNALYFLQKHYGVNIYCISPESPLCNYFPL                    162

CST-I  S-ININNNFTLENKHNNSINDILLTDNTPGVSFYKNQLKADNKIMLNFYNILHSKDNLIK                    296
HIN    SPLNNPITFILEEKKNYT-QDILI----PPKFVYK------KIGI--YSKPRIYQNLIF                    208

CST-I  FLNKEIAVLKKQTTQRAKARIQNHLSYKLGQALIINSKSVLGFLSLPFIILSIVISHKQE                    356
HIN    RLIWDILRLPNDIKHALKSRKWD                                                        231

CST-I  QKAYKFKVKKNPNLALPPLETYPDYNEALKEKECFTYKLGEEFIKAGKNWYGEGYIKFIF                    416

CST-I  KDVPRLKREFEKGE                                                                  430
```

LIPOPOLYSACCHARIDE α-2,3 SIALYTRANSFERASE OF *CAMPYLOBACTER JEJUNI* AND ITS USES

CROSS-REFERENCE TO RELATED APPLICATION

This application is a divisional of and claims benefit of U.S. application Ser. No. 09/272,960, filed Mar. 18, 1999, which claims the benefit of U.S. Provisional Application No. 60/078,891, filed Mar. 20, 1998 now abandoned, the disclosures of both of which are incorporated herein by reference, in their entirety for all purposes.

BACKGROUND OF THE INVENTION

1. Field of the Invention

This invention relates to the field of cloning and expression of sialyltransferase enzymes. In particular, the preferred sialyltransferases are bacterial transferases obtained from, for example, *Campylobacter jejuni*.

2. Background

Carbohydrates are now recognized as being of major importance in many cell-cell recognition events, notably the adhesion of bacteria and viruses to mammalian cells in pathogenesis and leukocyte-endothelial cell interaction through selectins in inflammation (Varki (1993) *Glycobiology* 3: 97–130). Moreover, sialylated glycoconjugates that are found in bacteria (Preston et al. (1996) *Crit. Rev. Microbiol.* 22:139–180; Reuter et al. (1996) *Biol. Chem. Hoppe-Seyler* 377:325–342) are thought to mimic oligosaccharides found in mammalian glycolipids to evade the host immune response (Moran et al. (1996) *FEMS Immunol. Med. Microbiol.* 16:105–115). Molecular mimicry of host structures by the saccharide portion of lipopolysaccharide (LPS) is considered to be a virulence factor of various mucosal pathogens, which use this strategy to evade a host immune response (Moran et al. (1996) *FEMS Immunol. Med. Microbiol.* 16: 105–115; Moran et al. (1996) *J. Endotoxin Res.* 3: 521–531).

One such pathogen, *Campylobacter jejuni,* is an important cause of acute gastroenteritis in humans (Skirrow (1977) *Brit. Med. J.* 2: 9–11). Epidemiological studies have shown that Campylobacter infections are more common in developed countries than Salmonella infections, and they are also an important cause of diarrheal diseases in developing countries (Ketley (1997) *Microbiol.* 143: 5–21). Moreover, *C. jejuni* infection has been implicated as a frequent antecedent to the development of Guillain-Barré syndrome, a form of neuropathy that is the most common cause of generalized paralysis (Ropper (1992) *N. Engl. J Med.* 326: 1130–1136). The *C. jejuni* serotype most commonly associated with Guillian-Barré syndrome is O:19 (Kuroki et al. (1993) *Ann. Neurol.* 33: 243–247). The core oligosaccharides of low molecular weight LPS of O:19 strains exhibit molecular mimicry of several gangliosides (Aspinall et al. (1994) *Biochemistry* 33: 241–249; Aspinall et al. (1994) *Biochemistry* 33: 250–255). Terminal oligosaccharide moieties identical to those of $GD_{1a}$, $GD_3$, $GM_1$ and $GT_{1a}$ gangliosides have been found in various O:19 strains. The significance of molecular mimicry as a virulence factor makes the identification of the genes involved in LPS synthesis and the study of their regulation of considerable interest for a better understanding of the pathogenesis mechanisms used by these bacteria.

The oligosaccharide structures involved in these and other processes are potential therapeutic agents, but they are time consuming and expensive to make by traditional chemical means. A very promising route to production of specific oligosaccharide structures is through the use of the enzymes which make them in vivo, the glycosyltransferases. Such enzymes can be used as regio- and stereoselective catalysts for the in vitro synthesis of oligosaccharides (Ichikawa et al. (1992) *Anal. Biochem.* 202: 215–238). Sialyltransferases are a group of glycosyltransferases that transfer sialic acid from an activated sugar nucleotide to acceptor oligosaccharides found on glycoproteins, glycolipids or polysaccharides. The large number of sialylated oligosaccharide structures has led to the characterization of many different sialyltransferases involved in the synthesis of various structures. Based on the linkage and acceptor specificity of the sialyltransferases studied so far, it has been determined that at least 13 distinct sialyltransferase genes are present in mammals (Tsuji et al (1996) *Glycobiology* 6:v–vii).

Large scale enzymatic synthesis of oligosaccharides depends on the availability of sufficient quantities of the required glycosyltransferases. However, production of glycosyltransferases in sufficient quantities for use in preparing oligosaccharide structures has been problematic. Expression of many mammalian glycosyltransferases has been achieved involving expression in eukaryotic hosts which can involve expensive tissue culture media and only moderate yields of protein (Kleene et al. (1994) *Biochem. Biophys. Res. Commun.* 201: 160–167; Williams et al. (1995) *Glycoconjugate J.* 12: 755–761). Expression in *E. coli* has been achieved for mammalian glycosyltransferases, but these attempts have produced mainly insoluble forms of the enzyme from which it has been difficult to recover active enzyme in large amounts (Aoki et al. (1990) *EMBO. J.* 9:3171–3178; Nishiu et al. (1995) *Biosci. Biotech. Biochem.* 59 (9): 1750–1752). Furthermore, because of the biological activity of their products, mammalian sialyltransferases generally act in specific tissues, cell compartments and/or developmental stages to create precise sialyloglycans.

Bacterial sialyltransferases are not subject to the same constraints and can use a wider range of acceptors than that of the mammalian sialyltransferases. For instance, the α-2,6-sialyltransferase from *Photobacterium damsela* has been shown to transfer sialic acid to terminal galactose residues which are fucosylated or sialylated at the 2 or 3 position, respectively (Kajihara et al. (1996) *J. Org. Chem.* 61:8632–8635). Such an acceptor specificity has not been reported so far for mammalian sialyltransferases. Despite their importance as proven or potential virulence factors, as well as their potential use in synthesizing sialylated oligosaccharides of interest, few bacterial sialyltransferases have been cloned (Weisgerber et al. (1991) *Glycobiol.* 1:357–365; Frosch et al. (1991) *Mol. Microbiol.* 5:1251–1263; Gilbert et al. (1996) *J. Biol. Chem.* 271:28271–28276) or purified (Yamamoto et al. (1996) *J. Biochem.* 120:104–110). The α-2,8-sialyltransferases involved in the synthesis of the polysialic acid capsules have been cloned and expressed from both *Escherichia coli* (Weisgerber et al. (1991) *Glycobiol.* 1:357–365) and *N. meningitidis* (Frosch et al. (1991) *Mol. Microbiol.* 5:1251–1263). Glycosyltransferases from *N. gonorrhoeae* which are involved in the synthesis of lipooligosaccharide (LOS) have been cloned (U.S. Pat. No. 5,545,553).

Thus, bacterial sialyltransferases would be useful in a number of applications, such as the synthesis of desired oligosaccharides with biological activity. Identification and characterization of new bacterial sialyltransferases would thus be useful in the development of these technologies. The present invention fulfills this and other needs.

SUMMARY OF THE INVENTION

The invention provides nucleic acid molecules that include a polynucleotide sequence that encodes an α2,3-sialyltransferase polypeptide. The α2,3-sialyltransferase polypeptide has an amino acid sequence that is at least about 75% identical to an amino acid sequence as set forth in SEQ. ID. NO:2 over a region at least about 50 amino acids in length when compared using the BLASTP algorithm with a wordlength (W) of 3, and the BLOSUM62 scoring matrix. The polynucleotide sequences are preferably at least about 75% identical to a polynucleotide sequence of a *Campylobacter jejuni* α2,3-sialyltransferase gene as set forth in SEQ. ID. NO:1 over a region at least about 120 nucleotides in length when compared using the BLASTN algorithm with a wordlength (W) of 11, M=5, and N=−4. The nucleic acid molecules of the invention will generally hybridize to a polynucleotide sequence of SEQ. ID. NO:1 under stringent conditions.

The invention also provides isolated α2,3-sialyltransferase polypeptides that have an amino acid sequence at least about 75% identical to the amino acid sequence of a *Campylobacter jejuni* α2,3-sialyltransferase as set forth in SEQ. ID. No.2, over a region at least about 50 amino acids in length, when compared using the BLASTP algorithm with a wordlength (W) of 3, and the BLOSUM62 scoring matrix. The invention provides, in one embodiment, full-length sialyltransferase polypeptides that have about 430 amino acids. Also provided are truncated sialyltransferase polypeptides that are at least about 328 amino acids in length and also have sialyltransferase activity.

In another embodiment, the invention provides cells that have a recombinant expression cassette containing a promoter operably linked to a polynucleotide sequence which encodes an α2,3-sialyltransferase polypeptide as described herein. Both prokaryotic and eukaryotic cells that express the sialyltransferase polypeptide are provided.

Another embodiment of the invention provides methods of adding a sialic acid residue to an acceptor molecule that has a terminal galactose residue. The methods involve contacting the acceptor molecule with an activated sialic acid molecule and an α2,3-sialyltransferase polypeptide of the invention. The terminal galactose residue of the acceptor is typically linked through a β linkage to a second residue in the acceptor molecule. Where the linkage between the terminal galactose residue and the second residue is a β1,4 linkage, the second residue is typically a Glc or a GlcNAc residue. Where the linkage is a β1,3 linkage, the second residue can be a GlcNAc or a GalNAc residue.

BRIEF DESCRIPTION OF THE DRAWINGS

FIG. 2 shows the nucleotide sequence (SEQ ID NO:1) and deduced amino acid sequence (SEQ ID NO:2) of the *C. jejuni* cst-I gene. Only the sequence encoding the cst-I gene is shown in this figure.

FIG. 3 shows an alignment of the deduced amino acid sequences of the *C. jejuni* OH4384 cst-I gene (CST-I; SEQ ID NO:2) and an *H. influenzae* putative ORF (HIN; SEQ ID NO:5) (GenBank #U32720). The alignment was performed using the ALIGN program (Genetics Computer Group, Madison Wis.). The solid vertical lines between the sequences show identical residues.

DESCRIPTION OF THE PREFERRED EMBODIMENTS

Definitions

Figure 1:
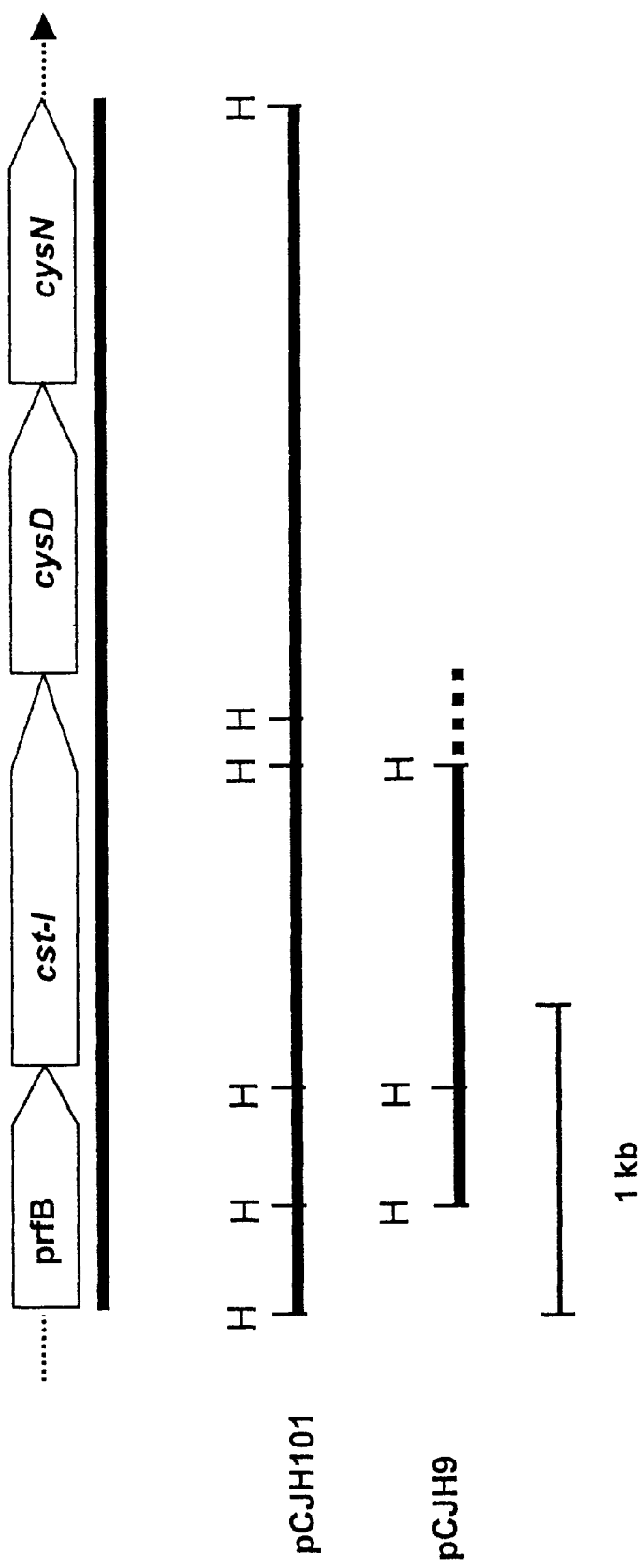
FIG. 1 shows a physical map and the genetic organization of the *C. jejuni* cst-I locus. The complete nucleotide sequence is shown in FIG. 2, and is available in GenBank as Accession No. AF130466. The insert of pCJH101 is 3.9 kb, while the insert of pCJH9 is 5.3 kb. Only the first 1.4 kb of pCJH9 is shown because the sequence downstream was found not to be contiguous in the *C. jejuni* OH4384 genome. HindIII sites are indicated ("H"). The partial prfB gene is similar to a peptide chain release factor (GenBank #AE000537) from *Helicobacter pylori*, while the cysD gene and the partial cysN gene are similar to *E. coli* genes that encode sulfate adenyltransferase subunits (GenBank #AE000358).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose or furanose.

A "sialyltransferase polypeptide" of the invention is sialyltransferase protein, or fragment thereof, that is capable of catalyzing the transfer of a sialic acid from a donor substrate (e.g., CMP-NeuAc) to an acceptor molecule. Typically, such polypeptides will be substantially similar to the exemplified proteins disclosed here. The addition of the sialic acid generally takes place at the non-reducing end of an oligosaccharide or carbohydrate moiety on a biomolecule. Biomolecules as defined here include but are not limited to biologically significant molecules such as carbohydrates, proteins (e.g., glycoproteins), and lipids (e.g., glycolipids, phospholipids, sphingolipids and gangliosides).

The sialyltransferases of the invention can be used to add sialic acid residues of different forms to acceptor molecules. Typically, the sialic acid is 5-N-acetylneurarninic acid, (NeuAc) or 5-N-glycolylneuraminic acid (NeuGc). Other sialic acids may be used in their place, however. For a review of different forms of sialic acid suitable in the present invention, see, Schauer, *Methods in Enzymology*, 50: 64–89 (1987), and Schaur, *Advances in Carbohydrate Chemistry and Biochemistry*, 40: 131–234.

| | |
|---|---|
| Ara = | arabinosyl; |
| Fru = | fructosyl; |
| Fuc = | fucosyl; |
| Gal = | galactosyl; |
| GalNAc = | N-acetylgalactosaminyl; |
| Glc = | glucosyl; |
| GlcNAc = | N-acetylglucosaminyl; |
| Man = | mannosyl; and |
| NeuAc = | sialyl (N-acetylneuraminyl). |

Additional abbreviations used are: LPS, lipopolysaccharide; LOS, lipooligosaccharide; CMP-Neu5Ac, cytidine monophosphate-N-acetylneuraminic acid; CE, capillary electrophoresis; LIF, laser induced fluorescence; FCHASE, 6-(5-fluorescein-carboxamido)-hexanoic acid succimidyl ester.

Donor substrates for glycosyltransferases are activated nucleotide sugars. Such activated sugars generally consist of uridine and guanosine diphosphate and cytidine monophosphate derivatives of the sugars in which the nucleoside diphosphate or monophosphate serves as a leaving group. The donor substrate for the sialyltransferases of the invention are activated sugar nucleotides that comprises the desired sialic acid. For instance, in the case of NeuAc, the activated sugar is CMP-NeuAc.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof. A "subsequence" refers to a sequence of nucleotides or amino acids that comprise a part of a longer sequence of nucleotides or amino acids (e.g., polypeptide), respectively.

The term "operably linked" refers to functional linkage between a nucleic acid expression control sequence (such as a promoter, signal sequence, or array of transcription factor binding sites) and a second polynucleotide, wherein the expression control sequence affects transcription and/or translation of the second polynucleotide.

A "heterologous sequence" or a "heterologous nucleic acid", as used herein, is one that originates from a source foreign to the particular host cell, or, if from the same source, is modified from its original form. Thus, a heterologous glycosyltransferase gene in a prokaryotic host cell includes a glycosyltransferase gene that, although being endogenous to the particular host cell, has been modified. Modification of the heterologous sequence can occur, e.g., by treating the DNA with a restriction enzyme to generate a DNA fragment that is capable of being operably linked to the promoter. Techniques such as site-directed mutagenesis are also useful for modifying a heterologous nucleic acid.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette" or simply an "expression cassette" is a nucleic acid construct, generated recombinantly or synthetically, that has control elements that are capable of effecting expression of a structural gene that is operably linked to the control elements in hosts compatible with such sequences. Expression cassettes include at least promoters and optionally, transcription termination signals. Typically, the recombinant expression cassette includes at least a nucleic acid to be transcribed (e.g., a nucleic acid encoding a desired polypeptide) and a promoter. Additional factors necessary or helpful in effecting expression can also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "isolated" is meant to refer to material which is substantially or essentially free from components which normally accompany the enzyme as found in its native state. Thus, when isolated, the enzymes of the invention do not include materials normally associated with their in situ environment. Typically, isolated sialyltransferases or sialyltransferase-encoding nucleic acids of the invention are at least about 80% pure, usually at least about 90%, and preferably at least about 95% pure as measured by band intensity on a silver stained gel or other method for determining purity. Protein purity or homogeneity can be indicated by a number of means well known in the art, such as polyacrylamide gel electrophoresis of a protein sample, followed by visualization upon staining. For certain purposes high resolution will be needed and HPLC or a similar means for purification utilized.

The terms "identical" or percent "identity," in the context of two or more nucleic acids or polypeptides, refer to two or more sequences or subsequences that are the same or have a specified percentage of nucleotides or amino acid residues that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 120 or 150 residues. In a most preferred embodiment, the sequences are substantially identical over the entire length of the coding regions or polypeptides.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example of algorithm that is suitable for determining percent sequence identity and sequence similarity is the BLAST algorithm, which is described in Altschul et al, *J. Mol. Biol.* 215:403–410 (1990). Software for performing BLAST analyses is publicly available through the National Center for Biotechnology Information (http://www.ncbi.nhn.m.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff& Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two nucleic acid sequences are substantially identical is that the two molecules hybridize to each other under stringent conditions. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence. The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide.

A further indication that two nucleic acid sequences or polypeptides are substantially identical is that the polypeptide encoded by the first nucleic acid is immunologically cross reactive with the polypeptide encoded by the second nucleic acid, as described below. The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, a specified antibody binds preferentially to a particular protein and does not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) *Antibodies, A Laboratory Manual,* Cold Spring Harbor Publications, New York, for a description of immunoassay formats and conditions that can be used to determine specific immunoreactivity.

A polypeptide is typically substantially identical to a second polypeptide, for example, where the two peptides differ only by conservative substitutions. A "conservative substitution," when describing a protein, refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. See, e.g., Creighton (1984) *Proteins,* W. H. Freeman and Company. In addition, individual substitutions, deletions or additions which alter, add or delete a single amino acid or a small percentage of amino acids in an encoded sequence are also "conservatively modified variations".

DESCRIPTION OF THE INVENTION

The present invention provides an α2,3 sialyltransferase from *Campylobacter jejuni.* Also provided are nucleic acids that encode the sialyltransferase, and methods of using the nucleic acids to produce the sialyltransferase.

Nucleic Acids Encoding α2,3-Sialyltransferases

The invention provides nucleic acid molecules that include a polynucleotide sequence that encodes an α2,3-sialyltransferase polypeptide that have an amino acid sequence that is at least about 75% identical to an amino acid sequence as set forth in SEQ ID NO:2. The region of identity is typically over a region at least about 50 amino acids in length when compared using the BLASTP algorithm with a wordlength (W) of 3, and the BLOSUM62 scoring matrix. The region of identity extends more preferably over at least about 200 amino acids, still more preferably over at least about 328 amino acids, and most preferably over the full length of the polypeptide.

The polynucleotide sequences are typically at least about 75% identical to a polynucleotide sequence of a *Campylobacter jejuni* α2,3-sialyltransferase gene such as that set forth in SEQ ID NO:1. The region of similarity between the nucleic acid molecules of the invention and the *C. jejuni* sialyltransferase sequence extends over at least about 120 nucleotides, preferably over at least about 500 nucleotides, and most preferably extends over the entire length of the sialyltransferase coding region. To identify nucleic acids of the invention, one can employ a nucleotide sequence comparison algorithm such as are known to those of skill in the art. For example, one can use the BLASTN algorithm. Suitable parameters for use in BLASTN are a wordlength (W) of 11, M=5, and N=−4. Alternatively, one can identify a nucleic acid of the invention by hybridizing, under stringent conditions, the nucleic acid of interest to a nucleic acid that includes a polynucleotide sequence of SEQ ID NO:1. One example of a nucleic acid of the invention includes a polynucleotide sequence of a *C. jejuni* α2,3-sialyltransferase enzyme as set forth in SEQ ID NO:1.

Nucleic acids of the invention can encode an entire sialyltransferase enzyme, or can encode a subsequence of a sialyltransferase gene. For example, the invention includes nucleic acids that encode a polypeptide which is not a full-length sialyltransferase enzyme, but nonetheless has sialyltransferase activity. A nucleic acid that encodes at least the amino terminal 328 amino acids of a *C. jejuni* α2,3-sialyltransferase as set forth in SEQ ID NO:2, for example, is provided by the invention, as are nucleic acids that encode the entire 430 amino acid sialyltransferase polypeptide. Nucleic acids that encode an α2,3-sialyltransferase having conservative substitutions of amino acids within the sequence of SEQ ID NO:2 are also provided by the invention.

The practice of this invention involves the construction of recombinant nucleic acids and the expression of genes in transfected host cells. Molecular cloning techniques to achieve these ends are known in the art. A wide variety of cloning and in vitro amplification methods suitable for the construction of recombinant nucleic acids such as expression vectors are well-known to persons of skill. Examples of these techniques and instructions sufficient to direct persons of skill through many cloning exercises are found in Sambrook et al. (1989) *Molecular Cloning: A Laboratory Manual*, 2nd Ed., Vols. 1–3, Cold Spring Harbor Laboratory; Berger and Kirnmel, *Guide to Molecular Cloning Techniques, Methods in Enzymology* volume 152 Academic Press, Inc., San Diego, Calif.; and *Current Protocols in Molecular Biology*, F. M. Ausubel et al., eds., *Current Protocols*, a joint venture between Greene Publishing Associates, Inc. and John Wiley & Sons, Inc., (1994 Supplement).

Nucleic acids that encode the sialyltransferase polypeptides of this invention can be prepared by any suitable method known in the art, including, for example, cloning and restriction of appropriate sequences or direct chemical synthesis by methods such as the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.*, 22: 1859–1862; and the solid support method of U.S. Pat. No. 4,458,066.

In one preferred embodiment, a nucleic acid encoding a sialyltransferase is isolated by routine cloning methods. A nucleotide sequence of a sialyltransferase-encoding gene or cDNA, as provided herein, is used to provide probes that specifically hybridize to a sialyltransferase cDNA in a cDNA library, a sialyltransferase gene in a genomic DNA sample, or to a sialyltransferase mRNA in a total RNA sample (e.g., in a Southern or Northern blot). Once the target sialyltransferase nucleic acid is identified, it can be isolated according to standard methods known to those of skill in the art.

The desired nucleic acids can also be cloned using well known amplification techniques. Examples of protocols sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3: 81–94; (Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077–1080; VanBrunt (1990) *Biotechnology* 8: 291–294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039. Suitable primers for use in the amplification of the nucleic acids of the invention include, for example:

```
CJ18F: 5' primer of C. jejuni α-2,3-STase
(SEQ ID NO:3) (41 mer, NdeI site in italics)

5' C TTA GGA GGT CAT ATG ACA AGG ACT AGA ATG GAA
AAT GAA C 3'

CJ40R: 3' primer of C. jejuni α-2,3-STase
(SEQ ID NO:4) with 6 His tail (60 mer, SalI site
in italics, (His)₆ (SEQ ID NO:6) tag in bold)

5' CC TAG GTC GAC TCA TTA GTG GTG ATG GTG GTG ATG
TTC CCC TTT CTC AAA CTC TCT CTT C 3'.
```

The sialyltransferase nucleic acids can also be cloned by detecting their expressed products by means of assays based on the physical, chemical, or immunological properties of the expressed proteins. For example, one can identify a cloned sialyltransferase nucleic acid by the ability of a polypeptide encoded by the nucleic acid to catalyze the transfer of a sialic acid from a donor to an acceptor moiety. In a preferred method, capillary electrophoresis is employed to detect the reaction products. This highly sensitive assay involves using either monosaccharide or disaccharide aminophenyl derivatives which are labeled with fluorescein as described below and in Wakarchuk et al. (1996) *J. Biol. Chem.* 271 (45): 28271–276.

In some embodiments, it may be desirable to modify the sialyltransferase nucleic acids of the invention. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) *Gene* 8:81–97, Roberts et al. (1987) *Nature* 328: 731–734.

α2,3-Sialyltransferase Enzymes

The invention also provides α2,3-sialyltransferase enzymes. The α2,3-sialyltransferase polypeptides of the invention typically have an amino acid sequence that is at least about 75% identical to an amino acid sequence of a *C. jejuni* α2,3-sialyltransferase as set forth in SEQ ID NO:2. The region of similarity between a *C. jejuni* sialyltransferase and a polypeptide of interest typically extends over a region at least about 50 amino acids in length, more preferably over at least about 200 amino acids, still more preferably over at least about 328 amino acids, and most preferably over the full length of the polypeptide. One example of an algorithm that is useful for comparing a polypeptide to the amino acid sequence of a *C. jejuni* α2,3-sialyltransferase is the BLASTP algorithm; suitable parameters include a wordlength (W) of 3, and the BLOSUM62 scoring matrix. One example of a sialyltransferase polypeptide of the invention has an amino acid sequence as set forth in SEQ ID NO:2.

The polypeptides of the invention include full-length sialyltransferase enzymes, as well as truncated polypeptides that retain sialyltransferase activity. For example, the invention provides polypeptides that include at least the amino terminal 328 amino acids of a *C. jejuni* α2,3-sialyltransferase as set forth in SEQ ID NO:2, as well as polypeptides of length up to and including the entire 430 amino acids of the *C. jejuni* α2,3-sialyltransferase polypeptide. The invention also includes polypeptides that have conservative substitutions of amino acids within the sequence of SEQ ID NO:2.

Expression Cassettes Encoding Sialyltransferases of the Invention

To obtain the α2,3-sialyltransferase polypeptides of the invention, one can incorporate the sialyltransferase-encoding polynucleotides of the invention into expression cassettes for high level expression in a desired host cell. A typical expression cassette contains a promoter operably linked to the desired DNA sequence. More than one sialyltransferase polypeptide can be expressed in a single prokaryotic cell by placing multiple transcriptional cassettes in a single expression vector, by constructing a gene that encodes a fusion protein consisting of more than one sialyltransferase, or by utilizing different selectable markers for each of the expression vectors which are employed in the cloning strategy.

In a preferred embodiment, the expression cassettes are useful for expression of sialyltransferases in prokaryotic host cells. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al. (1977) *Nature* 198: 1056), the tryptophan (trp) promoter system (Goeddel et al. (1980) *Nucleic Acids Res.* 8: 4057), the tac promoter (DeBoer et al. (1983) *Proc. Natl. Acad. Sci. U.S.A.* 80:21–25); and the lambda-derived PL promoter and N-gene ribosome binding site (Shimatake et al. (1981) *Nature* 292: 128). The particular promoter system is not critical to the invention, any available promoter that functions in prokaryotes can be used.

Either constitutive or regulated promoters can be used in the present invention. Regulated promoters can be advantageous because the host cells can be grown to high densities before expression of the sialyltransferase polypeptides is induced. High level expression of heterologous proteins slows cell growth in some situations. Regulated promoters especially suitable for use in *E. coli* include the bacteriophage lambda PL promoter, the hybrid trp-lac promoter (Amann et al. (1983) *Gene* 25: 167; de Boer et al. (1983) *Proc. Natl. Acad. Sci. USA* 80: 21, and the bacteriophage T7 promoter (Studier et al. (1986) *J. Mol. Biol.*; Tabor et al., (1985). These promoters and their use are discussed in Sambrook et al., supra.

For expression of sialyltransferase polypeptides in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in Bacillus in addition to *E. coli*. Promoters suitable for use in eukaryotic host cells are well known to those of skill in the art.

A ribosome binding site (RBS) is conveniently included in the expression cassettes of the invention that are intended for use in prokaryotic host cells. An RBS in *E. coli*, for example, consists of a nucleotide sequence 3–9 nucleotides in length located 3–11 nucleotides upstream of the initiation codon (Shine and Dalgarno (1975) *Nature* 254: 34; Steitz, *In Biological regulation and development: Gene expression* (ed. R. F. Goldberger), vol. 1, p. 349, 1979, Plenum Publishing, NY).

Translational coupling can be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See, Squires et. al. (1988) *J. Biol. Chem.* 263: 16297–16302.

The sialyltransferase polypeptides can be expressed intracellularly, or can be secreted from the cell. Intracellular expression often results in high yields. If necessary, the amount of soluble, active sialyltransferase polypeptide may be increased by performing refolding procedures (see, e.g., Sambrook et al., supra.; Marston et al. (1984) *Bio/Technology* 2: 800; Schoner et al. (1985) *Bio/Technology* 3:151). In embodiments in which the sialyltransferase polypeptides are secreted from the cell, either into the periplasm or into the extracellular medium, the DNA sequence is linked to a cleavable signal peptide sequence. The signal sequence directs translocation of the sialyltransferase polypeptide through the cell membrane. An example of a suitable vector for use in *E. coli* that contains a promoter-signal sequence unit is pTA1 529, which has the *E. coli* phoA promoter and signal sequence (see, e.g., Sambrook et al., supra.; Oka et al. (1985) *Proc. Natl. Acad. Sci. USA* 82: 7212; Talmadge et al. (1980) *Proc. Natl. Acad. Sci. USA* 77: 3988; Takahara et al. (1985) *J. Biol. Chem.* 260: 2670).

One of skill would recognize that modifications can be made to the sialyltransferases without diminishing their biological activity. Some modifications may be made to facilitate the cloning, expression, or incorporation of the catalytic domain into a fusion protein. Such modifications are well known to those of skill in the art and include, for example, the addition of codons at either terminus of the polynucleotide that encodes the catalytic domain to provide, for example, a methionine added at the amino terminus to provide an initiation site, or additional nucleotides placed on either terminus to create conveniently located restriction sites or termination codons or purification sequences.

The sialyltransferase polypeptides of the invention can also be produced as fusion proteins. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook et al., supra.). For certain applications, it may be desirable to cleave the non-sialyltransferase amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

To facilitate purification of the sialyltransferase polypeptides of the invention, the nucleic acids that encode the sialyltransferase polypeptides can also include a coding sequence for an epitope or "tag" for which an affinity binding reagent is available. Examples of suitable epitopes include the myc and V-5 reporter genes; expression vectors useful for recombinant production of fusion polypeptides having these epitopes are commercially available (e.g., Invitrogen (Carlsbad, Calif.) vectors pcDNA3.1/Myc-His and pcDNA3.1/V5-His are suitable for expression in mammalian cells). Additional expression vectors suitable for attaching a tag to the fusion proteins of the invention, and corresponding detection systems are known to those of skill in the art, and several are commercially available (e.g., FLAG™ (Kodak, Rochester, N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In *Genetic Engineering: Principles and Methods*, J. K. Setlow, Ed., Plenum Press, NY; commercially available from Qiagen (Santa Clarita, Calif.)). The maltose binding protein encoded by the malE gene of *E. coli* provides another suitable tag for use in purifying sialyltransferases of the invention; expression vectors for expressing polypeptides that include this tag, as well as amylose resins suitable for their purification are commercially avaliable (e.g., pMAL, New England Biolabs).

A suitable system for obtaining recombinant proteins from *E. coli* which maintains the integrity of their N-termini has been described by Miller et al. *Biotechnology* 7:698–704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

Expression of Sialyltransferases of the Invention

Sialyltransferases of the invention can be expressed in a variety of host cells, including *E. coli*, other bacterial hosts, yeast, and various higher eukaryotic cells such as the COS, CHO and HeLa cells lines and myeloma cell lines. Examples of useful bacteria include, but are not limited to, Escherichia, Enterobacter, Azotobacter, Erwinia, Bacillus, Pseudomonas, Klebsielia, Proteus, Salmonella, Serratia, Shigella, Rhizobia, Vitreoscilla, and Paracoccus. The recombinant protein gene will be operably linked to appropriate expression control sequences for each host. For *E. coli*, this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The expression vectors of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant sialyltransferase polypeptides can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology* Vol. 182: *Guide to Protein Purification*., Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

Uses of Sialyltransferases

The invention provides methods of using sialyltransferases produced using the methods described herein to prepare desired oligosaccharides (which are composed of two or more saccharides). The sialyltransferase reactions of the invention take place in a reaction medium comprising at least one sialyltransferase, a donor substrate, an acceptor sugar and typically a soluble divalent metal cation. The methods rely on a sialyltransferase to catalyze the addition of a sialic acid residue to a substrate saccharide. For example, the invention provides methods for adding sialic acid in an α2,3 linkage to a galactose residue, by contacting a reaction mixture comprising an activated sialic acid (e.g., CMP-NeuAc, CMP-NeuGc, and the like) to an acceptor moiety comprising a Gal residue in the presence of a sialyltransferase that has been prepared according to the methods described herein. The *C. jejuni*-derived sialyltransferases of the invention are capable of adding a sialic acid residue in an α2,3 linkage to saccharide acceptors that contain a terminal Gal residue. Examples of suitable acceptors include a terminal Gal that is linked to GlcNAc or Glc by a β1,4 linkage, and a terminal Gal that is β1,3-linked to either GlcNAc or GalNAc.

The term "sialic acid" refers to any member of a family of nine-carbon carboxylated sugars. The most common member of the sialic acid family is N-acetyl-neuraminic acid (2-keto-5-acetamindo-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550–11557; Kanamori et al. (1990) *J. Biol. Chem.* 265: 21811–21819. Also included are 9-substituted sialic acids such as a 9-O—$C_1$–$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki (1992) Glycobiology 2:

25–40; *Sialic Acids: Chemistry, Metabolism and Function*, R. Schauer, Ed. (Springer-Verlag, New York (1992). The synthesis and use of sialic acid compounds in a sialylation procedure is disclosed in international application WO 92/16640, published Oct. 1, 1992.

The sialyltransferase prepared as described herein can be used in combination with additional glycosyltransferases. For example, one can use a combination of sialyltransferase and galactosyltransferases. A number of methods of using glycosyltransferases to synthesize desired oligosaccharide structures are known. Exemplary methods are described, for instance, WO 96/32491, Ito et al. (1993) *Pure Appl. Chem.* 65:753, and U.S. Pat. Nos. 5,352,670, 5,374,541, and 5,545,553. In this group of embodiments, the enzymes and substrates can be combined in an initial reaction mixture, or preferably the enzymes and reagents for a second glycosyltransferase cycle can be added to the reaction medium once the first glycosyltransferase cycle has neared completion. By conducting two glycosyltransferase cycles in sequence in a single vessel, overall yields are improved over procedures in which an intermediate species is isolated. Moreover, cleanup and disposal of extra solvents and by-products is reduced.

The products produced by the above processes can be used without purification. However, it is sometimes preferred to recover the product. Standard, well known techniques for recovery of glycosylated saccharides such as thin or thick layer chromatography, or ion exchange chromatography. IL is preferred to use membrane filtration, more preferably utilizing a reverse osmotic membrane, or one or more column chromatographic techniques for the recovery. For instance, membrane filtration wherein the membranes have molecular weight cutoff of about 3000 to about 10,000 can be used to remove proteins. Nanofiltration or reverse osmosis can also be used.

The following example is offered to illustrate, but not to limit the present invention.

EXAMPLE

This Example describes the cloning and characterization of a gene encoding the *C. jejuni* α2,3 sialyltransferase of the invention, as well as characterization of the sialyltransferase. The sialyltransferase is involved in the addition of sialic acid to the lipopolysaccharide of *Campylobacter jejuni* OH4384. Cloning was achieved by the use of a highly sensitive screening procedure based on the expression of enzyme activity.

Two clones encoding sialyltransferase activity were obtained, one encoding a 430 amino acid polypeptide and a second one encoding only the first 328 amino acid residues of the same polypeptide. The truncated α-2,3-sialyltransferase was active, since we could detect activity when it was expressed in *Escherichia coli*. The enzyme activity was found in the membrane fraction of cell extracts in *C. jejuni* as well as in the recombinant *E. coli*. The truncated form of the protein was more soluble than the full length protein.

In order to facilitate purification of the enzyme for characterization, we constructed and purified a soluble form of the full length protein by fusion to the *E. coli* maltose binding protein (MPB). We surveyed the acceptor specificity with the purified MBP fusion using various chromophore- and fluorophore-labelled oligosaccharides. The *C. jejuni* α-2,3-sialyltransferase used terminal Gal acceptors that were β1→4 linked to either Glc or to GlcNAc. The enzyme also uses as an acceptor, terminal Gal that is β1→3 linked to either GlcNAc or to GalNAc. Structures with both the β1→4 and the β1→3 linked Gal acceptors are found in the outer core of *C. jejuni* OH4384 LPS.

The recombinant α-2,3-sialyltransferase was used to synthesize 1 mg of a sialyllactose derivative which was analyzed by NMR to confirm the position and configuration of the linkage between the sialic acid and the galactose residues.

Methods

Basic Recombinant DNA Methods

Genomic DNA isolation from *C. jejuni* OH4384 was performed as described previously (Gilbert et al. (1996) *J. Biol. Chem.* 271: 28271–28276). Plasmid DNA isolation, restriction enzyme digestions, purification of DNA fragments for cloning, ligations and transformations were performed as recommended by the enzyme supplier, or the manufacturer of the kit used for the particular procedure. PCR was performed with AmpliTaq™ DNA polymerase (Perkin Elmer, Branchburg, N.J.) or Pwo DNA polymerase (Boehringer Mannheim, Montreal, QB) as described by the manufacturers. Restriction and DNA modification enzymes were purchased from New England Biolabs Ltd. (Mississauga, ON). DNA sequencing was performed using an Applied Biosystems (Montreal, QB) model 370A automated DNA sequencer and the manufacturer's cycle sequencing kit.

Cloning and Sequencing of the α-2,3-sialyltransferase from *C. jejuni*

A genomic library was prepared using a partial HindIII digest of the chromosomal DNA of *C. jejuni* OH4384. The partial digest was purified on a QIAquick column (QIAGEN Inc., Chatsworth, Calif.) and ligated with HindIII-digested pBluescript SK-. The ligation mixture was used to electroporate *Escherichia coli* DH5α cells which were plated on LB medium with 150 μg/mL ampicillin, 0.05 mM IPTG and 100 μg/mL X-Gal (5-bromo-4-chloro-indolyl-β-D-galactopyranoside). White colonies were picked in pools of 100 and were resuspended in 1 mL of medium with 15% glycerol. Twenty μL of each pool were used to inoculate 1.5 mL of LB medium supplemented with 150 μg/mL ampicillin. After 2 h of growth at 37° C., IPTG was added to 1 mM and the cultures were grown for another 4 h 30 min. The cells were recovered by centrifugation, resuspended in 0.5 mL of 50 mM MOPS (pH7, 10 mM $MgCl_2$) and sonicated for 1 min (minimum power, 50% cycle). The extracts were assayed for sialyltransferase activity as described below except that the incubation time and temperature were 18 h and 32° C., respectively. The positive pools were plated, and 200 colonies were picked and tested for activity in pools of 10. Finally, the colonies of the positive pools were tested individually. This led to the isolation of two positive clones, pCJH9 (5.3 kb insert) and pCJH101 (3.9 kb insert). Using several sub-cloned fragments and custom-made primers, the inserts of the two clones were completely sequenced on both strands. The clones with individual HindIII fragments were also tested for sialyltransferase activity and the insert of the only positive one (a 1.1 kb HindIII fragment cloned in pBluescript SK-) was transferred to pUC118 using KpnI and PstI sites in order to obtain the insert in the opposite orientation with respect to the plac promoter.

Assays

Protein concentration was determined using the bicinchoninic acid protein assay kit (Pierce, Rockford, Ill.). For all of the enzymatic assays, one unit of activity was defined as the amount of enzyme that generated one μmol of product per minute. FCHASE-labelled oligosaccharides were prepared as described in Gilbert et al. (1997) *Eur. J Biochem.* 249: 187–194. p-Nitrophenol-glycosides (p-NP-glycosides) were obtained from Sigma-Aldrich.

The α-2,3-sialyltransferase activity was assayed at 37° C. using 1 mM Lac-FCHASE (6-(5-fluorescein-carboxamido)- hexanoic acid succimidyl ester), 0.2 mM CMP-Neu5Ac, 50 mM MOPS pH7, 10 mM MnCl$_2$ and 10 MM MgCl$_2$ in a final volume of 10 μL. After 5 min the reaction mixtures with fluorogenic acceptors were diluted with 10 mM NaOH and analyzed by capillary electrophoresis performed using the separation conditions as described previously (Gilbert et al. (1997) supra.).

Kinetic analysis of acceptors was performed at 37° C. with p-NP-glycosides at concentrations of 0.1 to 10 mM, with CMP-Neu5Ac at 1 mM. Kinetic analysis of the donor CMP-Neu5Ac was performed at a concentration of 20 μM to 1000 μM with p-NP-lactose at 5 mM. Care was taken to ensure that the level of acceptor conversion was between about 5–10% for acceptor kinetic assays.

For donor kinetics the amount of conversion of CMP-Neu5Ac was calculated from the amount of product formed compared to an internal standard of 10 μM p-NP-glucose added after the reaction. This peak was well resolved from the acceptor and product peaks. The reactions with p-NP-glycosides were stopped by addition of an equal volume of 2% SDS, 20 mM EDTA and heated to 75° C. for 3 minutes and then diluted 1:1 (or maximally 1:10 for 10 mM concentrations) with water. The samples were then analyzed by CE using a diode array detector scanning between 260 and 300 nm, with the peaks at detected at 290 nm. The peaks from the electropherograms were analyzed using manual peak integration with the P/ACE Station™ software. For rapid detection of enzyme activity, samples from the transferase reaction mixtures were examined by thin layer chromatography on silica-60 TLC plates (E. Merck) as described in Gilbert et al. (1996) supra.

Determination of the Linkage Specificity of the Sialyltransferase

A preparative sialyltransferase reaction was performed using an extract of *E. coli* BMH/pCJH9G and 1 mg of Lac-FCHASE as the acceptor. The reaction conditions were as described previously (Gilbert et al. (1997) *Eur. J. Biochem.*, supra.). The sample for NMR was freeze-dried and dissolved in D$_2$O three times prior to collection of the spectra. NMR data collection was performed with a Bruker AMX 600 spectrometer. Spectra were recorded at 340 K in 5 mm tubes at a concentration of one mg of sialylated Lac-FCHASE in 0.6 ml of D$_2$O. All NMR experiments and spectral analysis were performed as previously described (Pavliak et al. (1993) *J. Biol. Chem.* 268: 14146–14152).

Construction and Purification of Maltose Binding Protein Fusions of cst-I

The malE gene (GenBank #AE000476) without its signal peptide was obtained by PCR amplification from *E. coli* BMH genomic DNA using primers that added a BamHI restriction site on the 5' end and an NdeI site on the 3' end. These two restriction sites allowed the gene to be inserted in the expression vector pCW (Wakarchuk et al. (1994) *Protein Sci.* 3: 467–475) immediately in front of the cst-I gene with a Gly-Gly-Gly-His (SEQ ID NO:7) linker between the two domains. The fusion proteins were purified on commercially available amylose resin (New England Biolabs) using a protocol suggested by the manufacturer. Maltose was removed by dialysis of the eluted protein against 50 mM HEPES-NaOH pH 7.5.

Results

Cloning and Sequencing of the α-2,3-sialyltransferase from *C. jejuni*

The plasmid library made using an unfractionated partial HindIII digestion of chromosomal DNA from *C. jejuni* OH4384 yielded 2,600 white colonies which were picked in pools of 100. Two pools with sialyltransferase activity were obtained when extracts of IPTG induced cultures were screened for enzyme activity using Lac-FCHASE as the acceptor and TLC separation for the detection of the product. We used the same protocol to screen pools of 10 and then individual clones until we obtained two positive clones which were designated pCJH9 (5.3 kb insert) and pCJH101 (3.9 kb insert). These two clones were completely sequenced on both strands using a combination of sub-cloning and custom-made primers. The nucleotide sequence indicated that pCJH9 contains three internal HindIII sites while pCJH101 contains four internal HindIII sites. Open reading frame (ORF) analysis and PCR reactions with *C. jejuni* OH4384 chromosomal DNA indicated that the nucleotide sequences on either side of the HindHIII site at nucleotide #1440 in pCJH9 was not contiguous in the chromosomal DNA. The sequence downstream of nucleotide #1440 in pCJH9 was not further studied while the first 1439 nucleotides were found to be completely comprised within the sequence of pCJH101 (FIG. 1). The ORF analysis and PCR reactions with chromosomal DNA indicated that all of the pCJH101 HindIII fragments were contiguous in *C. jejuni* OH4384 chromosomal DNA.

Four ORFs, two partial and two complete, are found in the nucleotide sequence of pCJH101 (FIG. 1). The first 812 nucleotides encode a polypeptide that is 69% identical with the last 260 amino acid residues of the peptide chain release factor RF-2 (prfB gene, GenBank #AE000537) from *Helicobacter pylori*. The last base of the TAA stop codon of the chain release factor is also the first base of the ATG start codon of an open reading frame that spans nucleotides #812 to #2104 in pCJH101. This ORF was designated cst-I (Campylobacter sialyltransferase I) and encodes a 430 amino acid polypeptide (FIG. 2) that has some similarity to a putative ORF from *Haemophilus influenzae* (GeneBank #U32720, FIG. 3). The putative *H. influenzae* ORF encodes a 231 amino acid polypeptide that is 39% identical to the middle region of the Cst-I polypeptide (amino acid residues #80 to #330). The nucleotide sequence downstream of cst-I includes an ORF and a partial ORF that encode polypeptides that are similar (>60% identical) to the two subunits of the *E. coli* sulfate adenyltransferase (GenBank #AE000358).

In order to confirm that the cst-I ORF (nt #812–2104) encodes sialyltransferase activity we sub-cloned the 1.1 kb HindIII fragment that spans nt-#727 to 1791 in pUC118. This construct (pCJH9G) includes the last 83 nucleotides of the prfB gene and the first 979 nucleotides of the cst-I gene, and therefore encodes a truncated form of the Cst-I protein (328 amino acids). Activity was detected in IPTG induced cultures of *E. coli* only when the truncated cst-I gene was in the same orientation as the plac promoter of the vector. This construct was used to express the enzyme that was used in the determination of the linkage specificity and the survey of the sialyltransferase.

Determination of the Linkage Specificity of the Sialyltransferase.

The product of a preparative reaction using Lac-FCHASE as acceptor was examined by NMR in order to determine the linkage specificity of the sialyltransferase encoded by cst-I. Complete assignment of the NMR spectra of the sialylated product was achieved by $^1$H-$^1$H and $^1$H-$^{13}$C chemical shift correlation experiments (Table 1). The chemical shift data is consistent with the proposed structure, (Gilbert et al. (1996) supra.), the down field shifted values for the Gal-β C-3 and H-3 resonances compared to the unsubstituted analogues being indicative of the Neu5Ac-α-(2→3)-Gal-linkage.

TABLE 1

$^1$H and $^{13}$C NMR chemical shifts for the oligosaccharide moiety of Neu5Ac-α-(2→3)-Gal-β-(1→4)-Glc-FCHASE prepared using the recombinant α-2,3-sialyltransferase from *Campylobacter jejuni* OH4384

| Sugar | Position | H | C |
|---|---|---|---|
| Glc | 1 | 5.01 | 101.3 |
|  | 2 | 3.58 | 73.7 |
|  | 3 | 3.74 | 75.3 |
|  | 4 | 3.74 | 79.1 |
|  | 5 | 3.70 | 76.1 |
|  | 6 | 3.81 | 60.8 |
|  | 6' | 3.96 |  |
| Gal | 1 | 4.55 | 103.8 |
|  | 2 | 3.60 | 70.4 |
|  | 3 | 4.15 | 76.5 |
|  | 4 | 3.98 | 68.5 |
|  | 5 | 3.72 | 76.1 |
|  | 6 | 3.76 | 62.0 |
|  | 6' | 3.76 |  |
| Neu5Ac | $3_{ax}$ | 1.81 | 40.6 |
|  | $3_{eq}$ | 2.77 |  |
|  | 4 | 3.70 | 69.4 |
|  | 5 | 3.86 | 52.5 |
|  | 6 | 3.65 | 73.9 |
|  | 7 | 3.59 | 69.2 |
|  | 8 | 3.90 | 72.8 |
|  | 9 | 3.87 | 63.5 |
|  | 9' | 3.64 |  |
|  | NAc | 2.04 | 22.8 |

In Table 1, first order chemical shifts measured at 37° C. in D$_2$O are referenced to the methyl resonance of acetone (2.225 ppm for $^1$H and 31.07 ppm for $^{13}$C). For each sugar residue the $^1$H data is recorded in the left hand column and the $^{13}$C data is on the right column. Within experimental error, the chemical shift data for the amninophenyl-(6–5-(fluorescein-carboxamido)-hexanoic acid amide) moiety are the same as those previously reported (Gilbert et al. (1996) *J. Biol. Chem.* 271: 28271–28276).

Expression of the Recombinant Proteins

Each clone was examined for the optimal induction kinetics from 200 mL shake flask experiments (Table 2). The experiments were performed by taking small portions after induction of expression with IPTG and measuring the sialyltransferase activity using Lac-FCHASE as the acceptor and CMP-Neu5Ac as the donor. The samples were also analyzed by SDS-PAGE. The original clones CST-01 and CST-03 produced inducible sialyltransferase activity. To increase the expression levels of the sialyltransferase and to reduce the amount of enzyme activity associated with the membrane fraction, we made and tested maltose binding protein gene fusions with the truncated and full length cst-I gene. These fusion proteins exhibited significant amounts of sialyltransferase activity. The observed activity was less than would have been predicted based on the level of protein seen by coomassie blue staining, which may indicate that additional sialyltransferase activity can be obtained by subjecting the preparations to procedures for resolubilization of inclusion bodies and aggregates.

TABLE 2

Expression data from various constructs of the *C. jejuni* α-2,3-sialyltransferase.

| Gene Designation | Protein length (aa and mol. weight) | Expression level (U/L) at maximal induction time | Specific Activity of crude extracts (mU/mg) |
|---|---|---|---|
| CST-01 | 328 + (His)$_6$ mw 39,289 | 1.8 (6 h) | ~6 |
| CST-03 | 430 + (His)$_6$ mw 51,219 | 2.9 (~16 h) | 8 |
| CST-05 (CST-01 + MalE) | 703 + (His)$_6$ mw 80,418 | 21.7 (4 h) | 53 pure = 160 |
| CST-06 (CST-03 + MalE) | 805 + (His)$_6$ mw 92,348 | 31.5 (O/N + 4 h) | 41 pure = 56 |

Shake flask cultures were grown in the presence of IPTG and the maximal induction of enzyme was determined by assaying small scale extracts for sialyltransferase activity.

Survey of Oligosaccharide Acceptors for the α-2,3-sialyltransferase and Comparison with Another Bacterial α-2,3-sialyltransferase The acceptor specificity of the *C. jejuni* α-2,3-sialyltransferase was examined with a panel of p-NP-glycosides having both β1→4 and β1→3 linkages. The kinetic data for all of the acceptors was collected using the MBP-fusion protein of the full length sialyltransferase. The data for the acceptor specificity were collected first by assaying the enzyme at an acceptor concentration of 2.0 mM. The acceptor with the lowest activity was given the value of 1 for the comparison of activity. These reaction conditions were used in a comparison (Table 3) of the *C. jejuni* enzyme with the Lst protein from *N. meningitidis* (Gilbert et al. (1996) *J. Biol. Chem.* 271: 28271–28276). The *N. meningitidis* Lst protein was also a MBP protein fusion which was soluble and purified by affinity chromatography.

TABLE 3

Comparison of enzyme activity of malE-cst and malE-lst on p-nitrophenyl-glycosides.

| Acceptor | Relative Activity (CST-06) | $K_{m(app)}$ (CST-06) | Relative Activity (NST-33) |
|---|---|---|---|
| Gal-β-1,4-Glc Lactose | 4.9 mU/mg = 420 | 1.3 mM ± 0.12 | 7.8 mU/mg = 30 |
| Gal-β-1,4-GlcNAc N-acetyl-Lactosamine | 4.4 | 0.8 mM ± 0.2 | 18.8 |
| Gal-β-1,3-GlcNAc Lacto-N-biose | 5.8 | 2.9 mM ± 0.8 | 1 |
| Gal-β-1,3-GalNAc-α T-Antigen | 2.5 | 2.7 mM ± 0.1 | ND |
| Gal-α-1,4-Gal-β-Glc P$^k$ | 0 | ND | 5.6 |
| Gal-β | 1 | ND | 1.2 |

ND, not determined

Conclusions

To clone the α-2,3-sialyltransferase from *C. jejuni* OH4384, this experiment employed an activity screening strategy that was previously used to clone the α-2,3-sialyltransferase from *Neisseria meningitidis* (Gilbert et al. (1996) supra.). However, in this case, a plasmid library was constructed using unfractionated HindIII fragments from a chromosomal DNA digest. This procedure greatly simplified the construction of the library but carried the risk of cloning an incomplete gene if a HindIII site was present internally. Because the genome size of *C. jejuni* is relatively small, approximately 1.7 MB (Taylor (1992) *Ann. Rev. Microbiol.* 46: 35–64), a relatively small number of clones are required to give a representative library.

The activity screening yielded two clones which encoded sialyltransferase activity (FIG. 1). ORF analysis suggested that a 430 amino acid polypeptide is responsible for the sialyltransferase activity while the sub-cloning of a 1.1 HindIII fragment indicated that a truncated form (328 amino acids) retained enzymatic activity. Although the 104 amino acids at the C-terminus are dispensable for in vitro enzymatic activity, they might interact with other cell components in vivo either for regulatory purposes or for proper cell localization.

The specificity of the Cst-I enzyme that we measured with the p-NP-glycosides was consistent with the types of acceptors which are found in the LOS from *C. jejuni* OH4384. The activity on both β1→3 and β1→4 linked galactose was almost identical (Table 3), which suggests that this enzyme may be responsible for making both the sialyllactose and the GM1 type linkages in the LOS. The acceptor specificity of this enzyme was compared to the α-2,3-sialyltransferase from *N. meningitidis* which has been extensively characterized (Gilbert et al. (1996) supra., Gilbert et al. (1997) *Eur. J. Biochem.* 249: 187–194). The comparison confirms our previous observation that the enzyme from *N. meningitidis* has a marked preference for β1→4 linkages and that the activity of this enzyme on a-linked galactose was unique, as the Cst-I enzyme shows no detectable activity on this acceptor. The lack of primary sequence homology between these enzymes suggests their structures have evolved to specifically recognize the acceptors present within their respective genera.

A BLASTX search in GenBank with the cst-I sequence revealed some similarity to a putative *Haemophilus influenzae* ORF (GeneBank #U32720) with no defined function. Pair-wise alignment between the deduced amino acid sequences indicated 39% identity over the alignment window. The first 80 amino acids and last 100 amino acid residues of the cst-I α-2,3-sialyltransferase are absent in the *H. influenzae* homologue but the rest of the two sequences line up without having to introduce any major gap. The function of the *H. influenzae* ORF is unknown; based on its similarity to the cst-I sequence, the *H. influenzae* ORF could encode a sialyltransferase, possibly with a different specificity, or another type of glycosyltransferase that recognizes a similar acceptor.

The α-2,3-sialyltransferase encoded by cst-I was demonstrated to have a different acceptor specificity from the *N. meningitidis* lst α-2,3-sialyltransferase by its almost equal ability to sialylate substrates with a terminal Gal which is β(1→4)-linked to either Glc or GlcNAc and also substrates with a terminal Gal that is β-(1→3)-linked to either GlcNAc or GalNAc. This broad acceptor specificity demonstrates its utility, and makes it an attractive tool for chemo-enzymatic synthesis of sialylated oligosaccharides.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An isolated α-2,3-sialyltransferase polypeptide, wherein the α-2,3-sialyltransferase polypeptide catalyzes the transfer of a sialic acid from a donor substrate to an acceptor sugar,
and wherein the α-2,3-sialyltransferase polypeptide comprises amino acids 1–328 of SEQ ID NO:2.

2. The α-2,3-sialyltransferase polypeptide of claim 1, wherein the α-2,3-sialyltransferase polypeptide comprises amino acids 1–430 of SEQ ID NO:2.

3. The α-2,3-sialyltransferase polypeptide of claim 1, wherein the α-2,3-sialyltransferase polypeptide further comprises an amino acid tag.

4. The α-2,3-sialyltransferase polypeptide of claim 3, wherein the amino acid tag is a member selected from the group consisting of polyhistidine, maltose binding protein, myc, V-5, and FLAG.

5. A method of adding a sialic acid residue to an acceptor molecule comprising a terminal galactose residue, the method comprising contacting the acceptor molecule with an activated sialic acid molecule and an α2,3-sialyltransferase that comprises amino acids 1–328 of SEQ ID NO:2.

6. The method of claim 5, wherein the terminal galactose residue is linked through a linkage to a second residue in the acceptor molecule.

7. The method of claim 6, wherein the linkage is a β1,4 linkage.

8. The method of claim 7, wherein the second residue is a Glc or a GlcNAc.

9. The method of claim 6, wherein the linkage is a β1,3 linkage.

10. The method of claim 9, wherein the second residue is a GlcNAc or a GalNAc.

11. The method of claim 5, wherein the activated sialic acid is CMP-Neu5Ac.

12. The method of claim 5, wherein the β-2,3-sialyltransferase polypeptide comprises amino acids 1–430 of SEQ ID NO:2.

13. The method of claim 5, wherein the α-2,3-sialyltransferase polypeptide further comprises an amino acid tag.

14. The method of claim 5, wherein the amino acid tag is a member selected from the group consisting of polyhistidine, maltose binding protein, myc, V-5, and FLAG.

15. An isolated Campylobacter jejuni α-2,3-sialyltransferase polypeptide, wherein the α-2,3-sialyltransferase polypeptide catalyzes the transfer of a sialic acid from a donor substrate to an acceptor sugar, and
wherein the α-2,3-sialyltransferase polypeptide is expressed by an α-2,3-sialyltransferase nucleic acid which is amplified by PCR using a first primer comprising SEQ ID NO:3 and a second primer comprising SEQ ID NO:4.

* * * * *

SEQUENCE LISTING

```
<160> NUMBER OF SEQ ID NOS: 7

<210> SEQ ID NO 1
<211> LENGTH: 1293
<212> TYPE: DNA
<213> ORGANISM: Campylobacter jejuni
<220> FEATURE:
<221> NAME/KEY: CDS
<222> LOCATION: (1)..(1293)
<223> OTHER INFORMATION: Campylobacter jejuni OH4384 cst-I gene
      alpha2,3-sialyltransferase

<400> SEQUENCE: 1 atg aca agg act aga atg gaa aat gaa ctc att gtt agt aaa aat atg        48
Met Thr Arg Thr Arg Met Glu Asn Glu Leu Ile Val Ser Lys Asn Met
  1               5                  10                  15 caa aat ata atc ata gca gga aat gga cct agc cta aaa aat att aat        96
Gln Asn Ile Ile Ile Ala Gly Asn Gly Pro Ser Leu Lys Asn Ile Asn
             20                  25                  30 tat aaa aga ctg cct aga gaa tat gat gtt ttt agg tgt aac cag ttt       144
Tyr Lys Arg Leu Pro Arg Glu Tyr Asp Val Phe Arg Cys Asn Gln Phe
         35                  40                  45 tat ttt gaa gat aag tat tat tta gga aaa aag att aaa gca gta ttt       192
Tyr Phe Glu Asp Lys Tyr Tyr Leu Gly Lys Lys Ile Lys Ala Val Phe
     50                  55                  60 ttt aat cct ggt gtc ttt tta caa cag tat cac act gca aaa caa ctt       240
Phe Asn Pro Gly Val Phe Leu Gln Gln Tyr His Thr Ala Lys Gln Leu
 65                  70                  75                  80 ata cta aaa aat gag tat gaa ata aaa aat att ttt tgc tct aca ttt       288
Ile Leu Lys Asn Glu Tyr Glu Ile Lys Asn Ile Phe Cys Ser Thr Phe
                 85                  90                  95 aat tta cct ttt att gaa agc aat gat ttt tta cat caa ttt tat aat       336
Asn Leu Pro Phe Ile Glu Ser Asn Asp Phe Leu His Gln Phe Tyr Asn
```

-continued

| | | | | | | | | | | | | | | | | |
|---|---|---|---|---|---|---|---|---|---|---|---|---|---|---|---|---|
| | | 100 | | | | 105 | | | | 110 | | | | | | |
| ttt | ttc | ccc | gat | gca | aaa | ctt | ggc | tat | gaa | gtt | att | gaa | aac | ctt | aaa | 384 |
| Phe | Phe | Pro | Asp | Ala | Lys | Leu | Gly | Tyr | Glu | Val | Ile | Glu | Asn | Leu | Lys | |
| | | 115 | | | | 120 | | | | 125 | | | | | | |
| gaa | ttt | tat | gct | tat | ata | aaa | tac | aat | gaa | att | tat | ttc | aat | aaa | aga | 432 |
| Glu | Phe | Tyr | Ala | Tyr | Ile | Lys | Tyr | Asn | Glu | Ile | Tyr | Phe | Asn | Lys | Arg | |
| | 130 | | | | 135 | | | | 140 | | | | | | | |
| att | act | tcg | ggc | gtc | tat | atg | tgt | gca | att | gct | att | gca | tta | gga | tat | 480 |
| Ile | Thr | Ser | Gly | Val | Tyr | Met | Cys | Ala | Ile | Ala | Ile | Ala | Leu | Gly | Tyr | |
| 145 | | | | 150 | | | | 155 | | | | 160 | | | | |
| aaa | acc | atc | tat | tta | tgt | ggc | att | gat | ttt | tat | gaa | gga | gat | gtt | att | 528 |
| Lys | Thr | Ile | Tyr | Leu | Cys | Gly | Ile | Asp | Phe | Tyr | Glu | Gly | Asp | Val | Ile | |
| | | | | 165 | | | | 170 | | | | 175 | | | | |
| tat | cct | ttt | gaa | gct | atg | agt | aca | aat | ata | aaa | aca | atc | ttt | cct | gga | 576 |
| Tyr | Pro | Phe | Glu | Ala | Met | Ser | Thr | Asn | Ile | Lys | Thr | Ile | Phe | Pro | Gly | |
| | | | 180 | | | | 185 | | | | 190 | | | | | |
| ata | aaa | gat | ttc | aaa | cct | tca | aat | tgt | cat | tct | aag | gaa | tac | gat | ata | 624 |
| Ile | Lys | Asp | Phe | Lys | Pro | Ser | Asn | Cys | His | Ser | Lys | Glu | Tyr | Asp | Ile | |
| | | 195 | | | | 200 | | | | 205 | | | | | | |
| gaa | gca | tta | aaa | ttg | tta | aaa | tca | ata | tac | aaa | gtt | aat | atc | tac | gca | 672 |
| Glu | Ala | Leu | Lys | Leu | Leu | Lys | Ser | Ile | Tyr | Lys | Val | Asn | Ile | Tyr | Ala | |
| | 210 | | | | 215 | | | | 220 | | | | | | | |
| ttg | tgt | gat | gat | tct | att | ttg | gca | aat | cat | ttt | cct | tta | tca | att | aat | 720 |
| Leu | Cys | Asp | Asp | Ser | Ile | Leu | Ala | Asn | His | Phe | Pro | Leu | Ser | Ile | Asn | |
| 225 | | | | 230 | | | | 235 | | | | 240 | | | | |
| att | aat | aac | aat | ttc | act | tta | gaa | aat | aag | cat | aat | aat | tct | ata | aat | 768 |
| Ile | Asn | Asn | Asn | Phe | Thr | Leu | Glu | Asn | Lys | His | Asn | Asn | Ser | Ile | Asn | |
| | | | | 245 | | | | 250 | | | | 255 | | | | |
| gat | att | tta | ttg | act | gat | aat | act | cct | ggc | gta | agt | ttt | tat | aaa | aat | 816 |
| Asp | Ile | Leu | Leu | Thr | Asp | Asn | Thr | Pro | Gly | Val | Ser | Phe | Tyr | Lys | Asn | |
| | | | 260 | | | | 265 | | | | 270 | | | | | |
| caa | ctt | aaa | gct | gat | aat | aaa | att | atg | ctt | aat | ttt | tat | aat | att | ctt | 864 |
| Gln | Leu | Lys | Ala | Asp | Asn | Lys | Ile | Met | Leu | Asn | Phe | Tyr | Asn | Ile | Leu | |
| | | 275 | | | | 280 | | | | 285 | | | | | | |
| cat | tct | aaa | gat | aat | tta | att | aaa | ttt | tta | aac | aaa | gaa | att | gcg | gta | 912 |
| His | Ser | Lys | Asp | Asn | Leu | Ile | Lys | Phe | Leu | Asn | Lys | Glu | Ile | Ala | Val | |
| | 290 | | | | 295 | | | | 300 | | | | | | | |
| tta | aaa | aaa | caa | acc | act | caa | cga | gct | aaa | gca | aga | atc | caa | aac | cat | 960 |
| Leu | Lys | Lys | Gln | Thr | Thr | Gln | Arg | Ala | Lys | Ala | Arg | Ile | Gln | Asn | His | |
| 305 | | | | 310 | | | | 315 | | | | 320 | | | | |
| cta | tcc | tat | aaa | cta | gga | caa | gct | ttg | att | ata | aat | tct | aaa | agt | gta | 1008 |
| Leu | Ser | Tyr | Lys | Leu | Gly | Gln | Ala | Leu | Ile | Ile | Asn | Ser | Lys | Ser | Val | |
| | | | 325 | | | | 330 | | | | 335 | | | | | |
| tta | ggt | ttt | tta | tct | tta | cct | ttt | ata | ata | tta | agt | atc | gtt | att | tca | 1056 |
| Leu | Gly | Phe | Leu | Ser | Leu | Pro | Phe | Ile | Ile | Leu | Ser | Ile | Val | Ile | Ser | |
| | | | 340 | | | | 345 | | | | 350 | | | | | |
| cat | aaa | caa | gaa | caa | aag | gct | tat | aaa | ttt | aaa | gta | aag | aaa | aat | cca | 1104 |
| His | Lys | Gln | Glu | Gln | Lys | Ala | Tyr | Lys | Phe | Lys | Val | Lys | Lys | Asn | Pro | |
| | | 355 | | | | 360 | | | | 365 | | | | | | |
| aat | tta | gct | tta | cct | cct | tta | gaa | act | tat | cct | gat | tat | aat | gaa | gct | 1152 |
| Asn | Leu | Ala | Leu | Pro | Pro | Leu | Glu | Thr | Tyr | Pro | Asp | Tyr | Asn | Glu | Ala | |
| | 370 | | | | 375 | | | | 380 | | | | | | | |
| tta | aaa | gaa | aaa | gaa | tgt | ttt | act | tat | aaa | tta | gga | gaa | gaa | ttt | ata | 1200 |
| Leu | Lys | Glu | Lys | Glu | Cys | Phe | Thr | Tyr | Lys | Leu | Gly | Glu | Glu | Phe | Ile | |
| 385 | | | | 390 | | | | 395 | | | | 400 | | | | |
| aaa | gct | ggt | aag | aat | tgg | tat | ggg | gag | ggg | tat | atc | aaa | ttt | ata | ttc | 1248 |
| Lys | Ala | Gly | Lys | Asn | Trp | Tyr | Gly | Glu | Gly | Tyr | Ile | Lys | Phe | Ile | Phe | |
| | | | | 405 | | | | 410 | | | | 415 | | | | |
| aaa | gat | gtt | cct | agg | ttg | aag | aga | gag | ttt | gag | aaa | ggg | gaa | taa | | 1293 |

```
Lys Asp Val Pro Arg Leu Lys Arg Glu Phe Glu Lys Gly Glu
            420                 425                 430
```

<210> SEQ ID NO 2
<211> LENGTH: 430
<212> TYPE: PRT
<213> ORGANISM: Campylobacter jejuni

<400> SEQUENCE: 2

```
Met Thr Arg Thr Arg Met Glu Asn Glu Leu Ile Val Ser Lys Asn Met
  1               5                  10                  15

Gln Asn Ile Ile Ile Ala Gly Asn Gly Pro Ser Leu Lys Asn Ile Asn
                 20                  25                  30

Tyr Lys Arg Leu Pro Arg Glu Tyr Asp Val Phe Arg Cys Asn Gln Phe
             35                  40                  45

Tyr Phe Glu Asp Lys Tyr Tyr Leu Gly Lys Lys Ile Lys Ala Val Phe
         50                  55                  60

Phe Asn Pro Gly Val Phe Leu Gln Gln Tyr His Thr Ala Lys Gln Leu
 65                  70                  75                  80

Ile Leu Lys Asn Glu Tyr Glu Ile Lys Asn Ile Phe Cys Ser Thr Phe
                 85                  90                  95

Asn Leu Pro Phe Ile Glu Ser Asn Asp Phe Leu His Gln Phe Tyr Asn
             100                 105                 110

Phe Phe Pro Asp Ala Lys Leu Gly Tyr Glu Val Ile Glu Asn Leu Lys
         115                 120                 125

Glu Phe Tyr Ala Tyr Ile Lys Tyr Asn Glu Ile Tyr Phe Asn Lys Arg
     130                 135                 140

Ile Thr Ser Gly Val Tyr Met Cys Ala Ile Ala Ile Ala Leu Gly Tyr
145                 150                 155                 160

Lys Thr Ile Tyr Leu Cys Gly Ile Asp Phe Tyr Glu Gly Asp Val Ile
                165                 170                 175

Tyr Pro Phe Glu Ala Met Ser Thr Asn Ile Lys Thr Ile Phe Pro Gly
            180                 185                 190

Ile Lys Asp Phe Lys Pro Ser Asn Cys His Ser Lys Glu Tyr Asp Ile
        195                 200                 205

Glu Ala Leu Lys Leu Leu Lys Ser Ile Tyr Lys Val Asn Ile Tyr Ala
    210                 215                 220

Leu Cys Asp Asp Ser Ile Leu Ala Asn His Phe Pro Leu Ser Ile Asn
225                 230                 235                 240

Ile Asn Asn Asn Phe Thr Leu Glu Asn Lys His Asn Ser Ile Asn
                245                 250                 255

Asp Ile Leu Leu Thr Asp Asn Thr Pro Gly Val Ser Phe Tyr Lys Asn
            260                 265                 270

Gln Leu Lys Ala Asp Asn Lys Ile Met Leu Asn Phe Tyr Asn Ile Leu
        275                 280                 285

His Ser Lys Asp Asn Leu Ile Lys Phe Leu Asn Lys Glu Ile Ala Val
    290                 295                 300

Leu Lys Lys Gln Thr Thr Gln Arg Ala Lys Ala Arg Ile Gln Asn His
305                 310                 315                 320

Leu Ser Tyr Lys Leu Gly Gln Ala Leu Ile Asn Ser Lys Ser Val
                325                 330                 335

Leu Gly Phe Leu Ser Leu Pro Phe Ile Ile Leu Ser Ile Val Ile Ser
            340                 345                 350

His Lys Gln Glu Gln Lys Ala Tyr Lys Phe Lys Val Lys Lys Asn Pro
        355                 360                 365
```

```
Asn Leu Ala Leu Pro Pro Leu Glu Thr Tyr Pro Asp Tyr Asn Glu Ala
        370                 375                 380

Leu Lys Glu Lys Glu Cys Phe Thr Tyr Lys Leu Gly Glu Glu Phe Ile
385                 390                 395                 400

Lys Ala Gly Lys Asn Trp Tyr Gly Gly Tyr Ile Lys Phe Ile Phe
                405                 410                 415

Lys Asp Val Pro Arg Leu Lys Arg Glu Phe Glu Lys Gly Glu
                420                 425                 430

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence:CJ18F
      5' primer

<400> SEQUENCE: 3
cttaggaggt catatgacaa ggactagaat ggaaaatgaa c                    41

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence:CJ40R
      3' primer

<400> SEQUENCE: 4
cctaggtcga ctcattagtg gtgatggtgg tgatgttccc ctttctcaaa ctctctcttc  60

<210> SEQ ID NO 5
<211> LENGTH: 231
<212> TYPE: PRT
<213> ORGANISM: Haemophilus influenzae
<220> FEATURE:
<223> OTHER INFORMATION: Haemophilus influenzae Rd putative open reading
      frame (ORF)

<400> SEQUENCE: 5

Met Gln Leu Ile Lys Asn Asn Glu Tyr Glu Tyr Ala Asp Ile Ile Leu
1               5                   10                  15

Ser Ser Phe Val Asn Leu Gly Asp Ser Glu Leu Lys Lys Ile Lys Asn
                20                  25                  30

Val Gln Lys Leu Leu Thr Gln Val Asp Ile Gly His Tyr Tyr Leu Asn
            35                  40                  45

Lys Leu Pro Ala Phe Asp Ala Tyr Leu Gln Tyr Asn Glu Leu Tyr Glu
        50                  55                  60

Asn Lys Arg Ile Thr Ser Gly Val Tyr Met Cys Ala Val Ala Thr Val
65                  70                  75                  80

Met Gly Tyr Lys Asp Leu Tyr Leu Thr Gly Ile Asp Phe Tyr Gln Glu
                85                  90                  95

Lys Gly Asn Pro Tyr Ala Phe His His Gln Lys Glu Asn Ile Ile Lys
            100                 105                 110

Leu Leu Pro Ser Phe Ser Gln Asn Lys Ser Gln Ser Asp Ile His Ser
        115                 120                 125

Met Glu Tyr Asp Leu Asn Ala Leu Tyr Phe Leu Gln Lys His Tyr Gly
    130                 135                 140

Val Asn Ile Tyr Cys Ile Ser Pro Glu Ser Pro Leu Cys Asn Tyr Phe
145                 150                 155                 160
```

```
Pro Leu Ser Pro Leu Asn Asn Pro Ile Thr Phe Ile Leu Glu Glu Lys
            165                 170                 175

Lys Asn Tyr Thr Gln Asp Ile Leu Ile Pro Pro Lys Phe Val Tyr Lys
            180                 185                 190

Lys Ile Gly Ile Tyr Ser Lys Pro Arg Ile Tyr Gln Asn Leu Ile Phe
        195                 200                 205

Arg Leu Ile Trp Asp Ile Leu Arg Leu Pro Asn Asp Ile Lys His Ala
    210                 215                 220

Leu Lys Ser Arg Lys Trp Asp
225                 230

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence:6 His tail
      (His)6

<400> SEQUENCE: 6

His His His His His His
 1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:linker
      between two fusion protein domains

<400> SEQUENCE: 7

Gly Gly Gly His
 1
```